United States Patent [19]

Rodriguez

[11] Patent Number: 4,944,738
[45] Date of Patent: * Jul. 31, 1990

[54] SURGICAL LASER BACKSTOP INSTRUMENT

[76] Inventor: Michael A. Rodriguez, 929 Graham Dr., Suite B, Tomball, Tex. 77375

[*] Notice: The portion of the term of this patent subsequent to Mar. 28, 2006 has been disclaimed.

[21] Appl. No.: 327,016

[22] Filed: Mar. 22, 1989

Related U.S. Application Data

[63] Continuation-in-part of Ser. No. 107,058, Oct. 13, 1987, Pat. No. 4,815,461.

[51] Int. Cl.$^5$ .............................................. A61B 17/36
[52] U.S. Cl. .......................................................... 606/2
[58] Field of Search ........................................ 128/4–8, 128/303 R, 303.1, 395–398; 606/1, 2

[56] References Cited

U.S. PATENT DOCUMENTS

| | | | |
|---|---|---|---|
| 1,283,189 | 10/1918 | Houck | 128/11 |
| 3,865,113 | 2/1975 | Sharon et al. | 128/303.1 |
| 3,982,541 | 9/1976 | L'Esperance | 128/303.1 |
| 4,178,920 | 12/1979 | Cawood et al. | 128/6 |
| 4,249,533 | 2/1981 | Komiya | 128/303.1 |
| 4,313,431 | 2/1982 | Frank | 128/7 |
| 4,492,230 | 1/1985 | Sunago et al. | 128/303.1 |
| 4,638,800 | 1/1987 | Michel | 128/303.1 |
| 4,646,734 | 3/1987 | Cabrera et al. | 128/303.1 |
| 4,648,892 | 3/1987 | Kittrell et al. | 128/303.1 |
| 4,815,461 | 3/1989 | Rodriguez | 128/303.1 |

FOREIGN PATENT DOCUMENTS

| | | | |
|---|---|---|---|
| 0070459 | 1/1983 | European Pat. Off. | 128/303.1 |
| 3209444 | 10/1982 | Fed. Rep. of Germany | 128/303.1 |

*Primary Examiner*—Max Hindenburg
*Attorney, Agent, or Firm*—Harrison & Egbert

[57] ABSTRACT

A surgical laser backstop instrument comprising a rod, a backstop pivotally mounted to one end of the rod, and a backstop adjustment mechanism mounted to the other end of the rod. The backstop is comprised of a non-reflective material. The backstop adjustment mechanism controls the movement of the backstop. The backstop is a flat section of titanium-coated material and is movable between a position longitudinally aligned with the axis of the rod and a position transverse to the axis of the rod. The backstop adjustment mechanism comprises a body connected to the other end of the rod, a line fastened at one end to the backstop and extending through the rod, and a movement actuator mechanism connected to the other end of the line for controlling the pivotal movement of the backstop. This movement actuator mechanism includes a knob rotatably mounted to the body, a rack assembly placed within the body and connected to the end of the line, and a pinion gear engaging the rack assembly and connected to the knob such that rotational movement of the knob causes movement of the rack assembly.

18 Claims, 3 Drawing Sheets

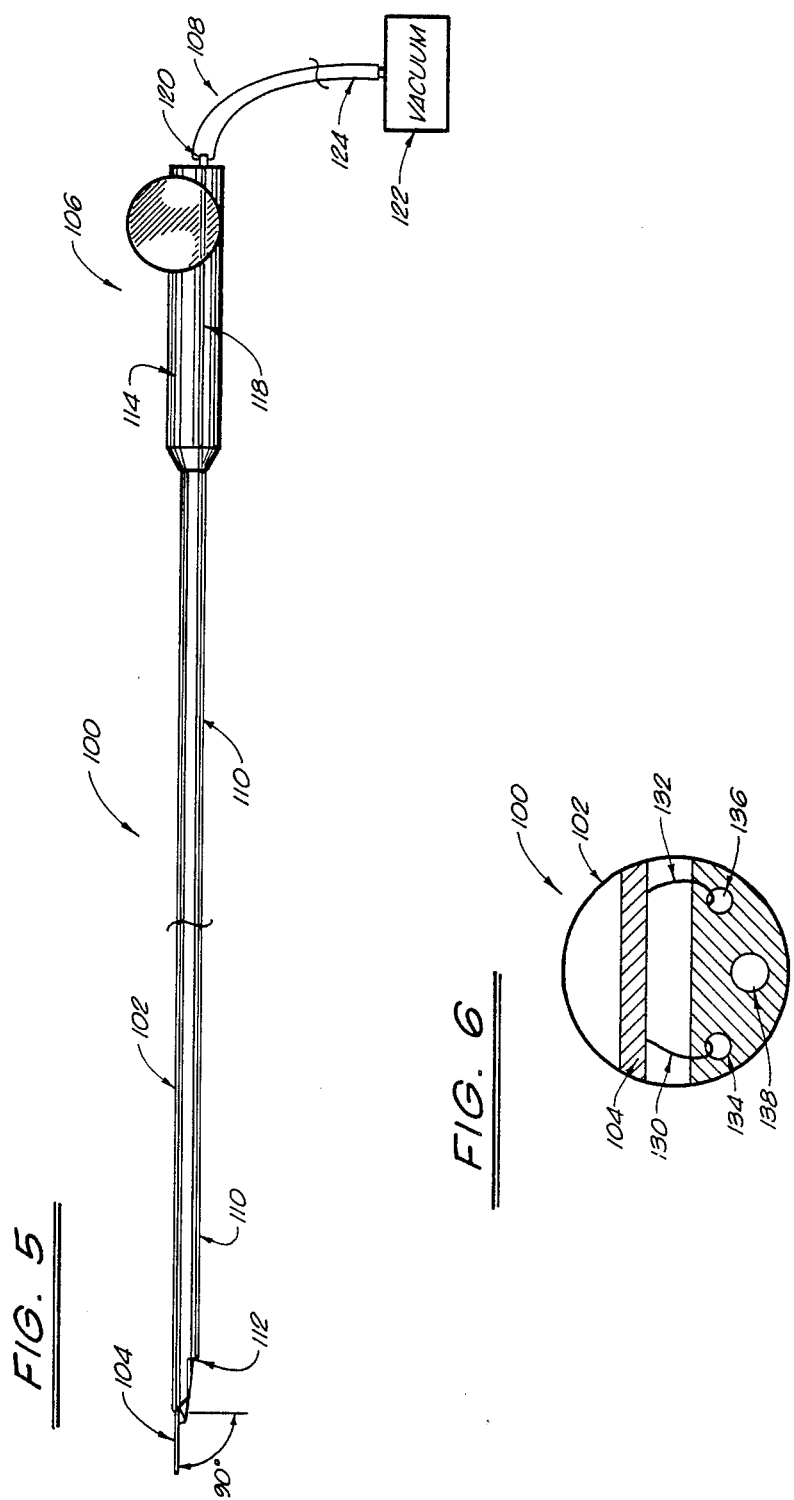

SURGICAL LASER BACKSTOP INSTRUMENT

Related Applications

The present invention is a continuation-in-part of U.S. application Ser. No. 107,058, filed on Oct. 13, 1987, entitled "Surgical Laser Backstop Instrument", now U.S. Pat. No. 4,815,461.

FIELD OF THE INVENTION

The present invention relates to surgical laser backstops. More particularly, the present invention relates to the use of lasers in a surgical procedure known as laparoscopy.

BACKGROUND OF THE INVENTION

A relatively new area of surgical procedure is known as laparoscopy. Lapaproscopy is the visual examination of the interior of the abdomen by the use of a laparoscope. A laparoscope is a long slender instrument for insertion through the abdominal wall. Through appropriate optical techniques, the surgeon is able to view the interior of the peritoneal cavity by proper use of the laparoscope.

This laparoscopy procedure is facilitated by the use of a trocar instrument. After the trocar instrument is inserted into the abdominal wall at two separate points, the pointed portion of the trocar is removed and a sleeve portion remains. The sleeve portion extends through the abdominal wall and communicates with the interior of the peritoneal cavity. In this surgical procedure, one of the trocar sleeves is placed for the purpose of allowing the insertion of the laparoscope. The other of the trocar sleeves is in position to allow the surgeon to insert an instrument for the manipulation of the internal organs for better viewing with the laparoscope.

After the surgeon has found adhesions during his use of laparoscopy, it is necessary to remove these adhesions by one technique or another. A recent development in laparoscopy has been the use of a laser beam for the removal of these adhesions. Typically, the laser is connected to and aligned with the laparoscope. The laser beam will have a suitable power for the removal of the adhesions found within the peritoneal cavity.

In order for a laser to be appropriately utilized in such surgery, it is necessary to have a laser backstop positioned adjacent to the adhesions being removed. This backstop may be inserted through the trocar sleeve and, through the use of the laparoscope, is positioned on the opposite side of the adhesion from the laser beam. It is important that the laser be directed to the appropriate location and that the laser does not cause any damage to internal organs other than to the adhesions.

At present, such laser backstops comprise a long slender rod with a fixed, longitudinally aligned backstop portion. Typically, adhesions will have a multitude of varied configurations. Many times, it is difficult to position the backstop so as to fully remove the adhesion. Since a fixed backstop does not "wrap around" or otherwise follow the contour of the adhesion, it is difficult to properly guide the laser beam so as to fully remove the adhesion.

Another problem with this laser surgery is that smoke, produced by the destruction of the adhesion, will interfere with the viewing capability of the laparoscope. Since the smoke does not dissipate immediately, the surgeon must proceed with the laser surgery even though viewing is somewhat obstructed.

It is an object of the present invention to provide a laser backstop instrument which is adjustable to follow the contour of the adhesion and to aid in the manipulation of the instrument in the peritoneal cavity.

It is another object of the present invention to provide a laser backstop instrument that assists in the removal of smoke during laser surgery.

It is still a further object of the present invention to provide a laser backstop that the surgeon can suitably manipulate to assist in the surgical procedure.

These and other objects and advantages of the present invention will become apparent from a reading of the attached specification and appended claims.

SUMMARY OF THE INVENTION

The present invention is a surgical laser backstop instrument that comprises a rod, a backstop pivotally mounted to one end of the rod, and a backstop adjustment mechanism mounted to the other end of the rod. The backstop is comprised of a non-reflecting material. The backstop adjustment mechanism serves to control the movement of the backstop relative to the position of the rod.

The rod is coated with a non-reflective material. Specifically, the rod is coated with titanium. The rod has a length of greater than twelve inches (12") and a diameter of greater than thirteen sixty-fourths of an inch (13/64"). Additionally, the rod has an evacuation bore extending longitudinally therethrough.

The backstop is a flat section of titanium-coated material having a width not greater than the diameter of the rod. This backstop is movable between a position in which the backstop is aligned with the longitudinal axis of the rod and a position in which the backstop is transverse to the longitudinal axis of the rod. The backstop extends outwardly from the end of the rod a distance of greater than seven-tenths of an inch (7/10").

The backstop adjustment mechanism comprises a body connected to the opposite end of the rod. A line is fastened to one end of the backstop and extends through a bore in the rod. A movement actuator mechanism is connected to the other end of the line for controlling the pivotal movement of the backstop. The body comprises a barrel having an aperture extending at least partially therethrough. This barrel is fixedly attached to the end of the rod. The line comprises a wire connected at one end of the movement actuator mechanism and at the other end to the backstop. This wire extends through the bore in the rod. Specifically, a pair of wires extends through parallel bores in the rod.

The movement actuator mechanism comprises a knob, a rack assembly, and a pinion gear. The knob is rotatably mounted to the body and serves to manually control the position of the backstop. The rack assembly is placed within the body and is connected to the other end of the line. The pinion gear engages the rack assembly and is connected to the knob such that a rotational movement of the knob causes a corresponding rotation of the pinion gear. The rotation of the pinion gear causes the rack assembly to be movable relative to the rotation of the pinion gear.

The present invention also includes smoke evacuation means. This smoke evacuation means comprises a vacuum communicating with the end of the evacuation bore in the rod. The vacuum serves to draw smoke through the evacuation bore. One end of the evacuation bore is generally adjacent the backstop. The body includes an aperture extending therethrough which is a continuation of this evacuation bore from the rod. As smoke is generated by the vaporization of tissue by the laser, the smoke is drawn from the peritoneal cavity, through the evacuation bore, and toward the vacuum pump.

BRIEF DESCRIPTION OF THE DRAWINGS

FIG. 5 is a cross-sectional side view showing the surgical laser backstop instrument, along with the smoke evacuation bore, in accordance with an alternative embodiment of the present invention.

FIG. 6 is an end view of the backstop portion of the alternative embodiment of the present invention.

DETAILED DESCRIPTION OF THE INVENTION

Figure 1:
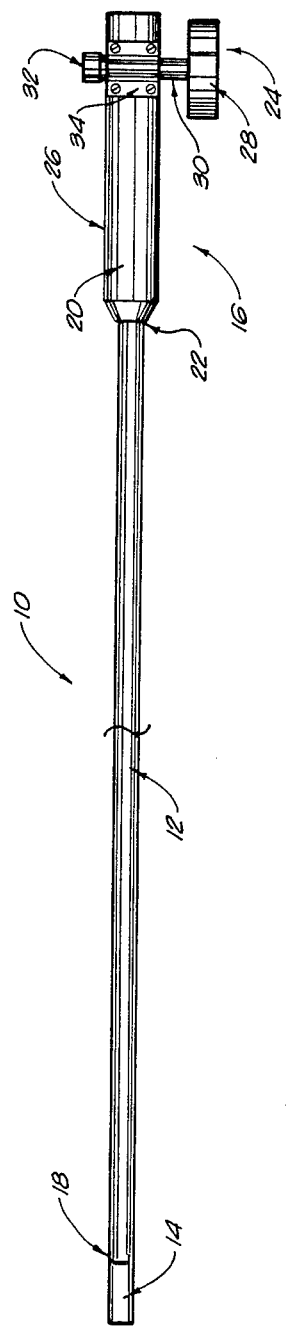
FIG. 1 is a top view of the surgical laser backstop instrument in accordance with the preferred embodiment of the present invention.

Referring to FIG. 1, there is shown at 10, the surgical laser backstop instrument in accordance with the preferred embodiment of the present invention. The surgical laser backstop instrument 10 comprises a rod 12, a backstop 14, and a backstop adjustment mechanism 16.

Rod 12 has a generally cylindrical shape and extends for a distance of greater than twelve inches (12"). Rod 12 also has a diameter of thirteen sixty-fourths of an inch (13/64") or greater. In surgery, these dimensions are rather important. The rod 12 should have a length greater than twelve inches (12") because such a length is important in carrying out proper surgical procedures. In order to properly penetrate and explore the peritoneal cavity, the rod should have a length of greater than twelve inches (12"). The diameter of rod 12 is also important since the diameter should be a close, nearly air-tight, match of the interior diameter of the trocar sleeve. Insofar as it is necessary to inflate the peritoneal cavity in order to properly use the laparoscope, it is also necessary, to some extent, to maintain an air-tight seal between the instrument and the interior of the trocal sleeve. If the rod had a dimension of less than thirteen sixty-fourths of an inch (13/64"), then there would be less than an airtight seal. This would cause the peritoneal cavity to deflate and to hamper the surgical procedure.

Rod 12 should be coated with a non-reflective material. Specifically, the rod should be coated with titanium material. It is important that a rod be coated with a laser non-reflective material since as any reflection caused by the interaction of the laser beam upon the rod could deflect the laser beam and cause potential damage to organ within the peritoneal cavity. Rod 12 has backstop 14 pivotally connected at one end and has the backstop adjustment mechanism 16 mounted at the other end. As will be described hereinafter, rod 12 may also include an evacuation bore which extends longitudinally therethrough.

Backstop 14 is pivotally mounted at 18 to rod 12. Backstop 14 is coated with a laser non-reflective material. Specifically, this laser non-reflective material is titanium, or a titanium-coated material. Backstop 14 has the width not greater than the diameter of rod 12. Since the instrument 10 must be inserted through the trocar sleeve, the width of backstop 14 must be less than the diameter of rod 12 so as to enhance the ability to insert the instrument 10 through the trocar sleeve and to enhance the ability to remove the instrument 10 from the trocar sleeve. Backstop 14 extends outwardly for a distance of greater than seven-tenths of an inch ("7/10") from the end 18 of the rod 12. It may be also possible to have a longer backstop for use in situations where the laser beam must be directed to a longer adhesion, or along a longer path. The length of the backstop is a balance between the convenience of use, the requirements of the laser operation, and the ability to manipulate the instrument in the peritoneal cavity.

As shown in FIG. 1, the backstop adjustment mechanism 16 includes a body 20 which is connected to the end 22 of rod 12. A movement actuator mechanism 24 is rotatably mounted with respect to the body 20. The movement actuator mechanism serves to cause the movement of the backstop 14, to be described hereinafter. Body 20 comprises a barrel, or handle 26, which includes an aperture (not shown) extending at least partially therethrough. Barrel 26 is fixedly attached to end 22 of rod 12.

As shown in FIG. 1, the movement actuator mechanism 24 is shown as a knob 28, an axle 30, and a cap nut 32. Movement actuator mechanism 24 is rotatably mounted to body 20 by bearing block 34. The movement actuator mechanism 24 also includes the internal mechanism within body 20 that is used to cause movement of the backstop 14 from the remote position of body 20. The backstop adjustment mechanism, as shown in FIG. 1, is made of chrome-plated brass.

Figure 2:
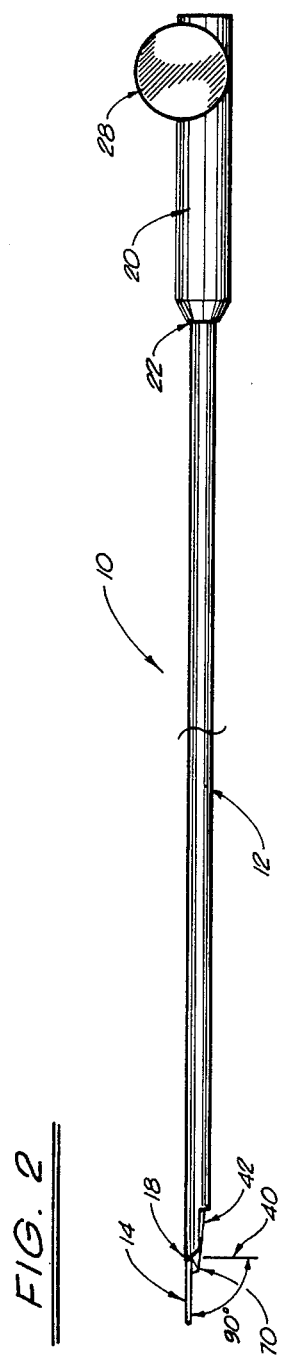
FIG. 2 is a side view showing the surgical laser backstop instrument in accordance with the preferred embodiment of the present invention.

FIG. 2 is a side view showing the surgical laser backstop instrument 10. As can be seen, backstop 14 is a rather thin titanium surface that is pivotally mounted at 18 to rod 12. Backstop 14 is movable for a ninety degree (90°) range of motion. This allows the backstop 14 to be movable between a position in which the backstop 14 is aligned with the longitudinal axis of rod 12 and a position in which the backstop 14 is transverse, in position 40, to the longitudinal axis of rod 12. As shown in FIG. 2, wire 42 extends outwardly from the interior of rod 12 and is fastened to backstop 14 at a position adjacent to the pivot point 18. Wire 42 passes through a longitudinal bore extending through rod 12. The forward and backward movement of wire 42 causes the pivotal movement of backstop 14 throughout the range of motion illustrated in FIG. 2. Also, in FIG. 2, it can be seen that the knob 28 is circular and is located at the rearward portion of body 20.

Figure 4:
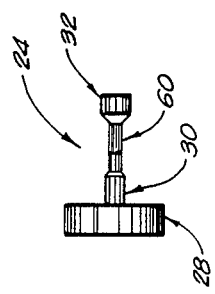
FIG. 4 shows the pinion gear and knob as contained within the body of the instrument.
Figure 3:
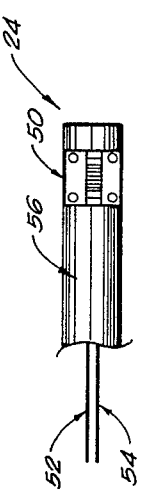
FIG. 3 is a sectional view showing the rack assembly contained within the body of the instrument.

FIGS. 3 and 4 show, in detail, the internal mechanism of the movement actuator mechanism 20. FIG. 3 shows rack assembly 50 which is located and positioned within body 20. As can be seen, a pair of wires 52 and 54 are fastened to attachment point 56 on rack assembly 50. In comparison with the instrument illustrated in FIG. 2, the wire 42 is actually a pair of wires 52 and 54 extending through parallel bores in rod 12. These wires also extend through the aperture of body 20.

FIG. 4 illustrates another aspect of the movement actuator mechanism 24. FIG. 4 shows an isolated end view of the knob 28, axle 30, and cap nut 32. Importantly, a pinion gear 60 is interposed between the cap nut 32 and the knob 28. Pinion gear 60 is positioned within the interior of body 20 and engages the teeth of rack assembly 50. Pinion gear 60 is connected to knob 28 such that the rotational movement of the knob 28 causes a corresponding rotational movement of the pinion gear 60. In combination with the rack assembly 50, the movement of the pinion gear 60 causes backward and forward movement of the rack assembly 50. The backward and forward movement of the rack assembly 50, therefore, causes a corresponding backward and forward movement of wires 52 and 54. As the wires 52 and 54 are drawn backward and forward, the backstop 14 is, as a result, moved about its pivoted axis between the positions illustrated in FIG. 2. The amount of angular movement of backstop 14 is controlled by the amount of rotation applied to the knob 28. Referring to FIG. 2, a stop 70 will abut a surface of rod 12 when the backstop 14 reaches position 40. This serves to limit the range of movement of the backstop 14 and serves to prevent the further rotation of the knob 28.

FIG. 5 illustrates an alternative embodiment of the present invention. FIG. 5 shows the surgical laser backstop instrument 100 having rod 102, backstop 104, movement actuator mechanism 106, and a smoke evacuation mechanism 108. For the most part, the configuration of the embodiment of FIG. 5 is identical to that described in connection with FIGS. 1–4. Importantly, however, the embodiment of FIG. 5 incorporates the smoke evacuation mechanism for the removal of smoke produced as a result of the laser surgery. Insofar as smoke is generally produced at the area of backstop 14 as a result of the laser surgery, the smoke evacuation mechanism 108 serves to draw the smoke from within the peritoneal cavity through the rod 102 and outwardly from the end of the instrument 100. Specifically, the smoke evacuation mechanism 108 includes an additional smoke evacuation bore 110 has an opening at 112 generally adjacent the backstop 104. The body 114 of the backstop adjustment mechanism 106 similarly has an aperture 118 extending therethrough. The aperture 118 communicates with the bore 110 and opens at the exterior 120 of the body 114. A vacuum pump 122 is connected by suitable means 124, such as tubes, hoses, or other means. Vacuum pump 122 produces a small vacuum that serves to draw the smoke from the area about backstop 104 into the opening 112, through the evacuation bore 110, through the aperture 118, and out through the exit opening 120.

FIG. 6 is an end view of the instrument 100. As can be seen, rod 102 has a circular configuration. The backstop 104 has lines 130 and 132 attached thereto. Lines 130 and 132 pass through bores 134 and 136 in the rod 102. The smoke evacuation bore 138 opens as illustrated in FIG. 6.

The present invention offers a number of advantages not found in the prior-art techniques of laser backstops in laparoscopy and laser surgery. In prior-art techniques, the backstop was a fixed, solid rod. In actual use, this makes it difficult to place the backstop along the contour of the to-be-removed adhesion. During surgical procedures, it is necessary for surgeons to utilize the laser for a portion of the adhesion, to remanipulate the backstop, to reactivate the laser, and carry out a number of steps in order to properly attack a single adhesion. On the other hand, by the proper adjustment of the adjustable laser backstop of the instrument of the present invention, the backstop can be placed so as to offer a continuous laser backstop along the length and contour of the adhesion in the peritoneal cavity. This greatly increases the ability to surgically remove the adhesion through laser technology.

The present invention also offers a longer backstop for laser surgery. Since it is possible to angularly adjust the backstop relative to the rod, a longer backstop can be utilized in the surgery. This permits a longer and more continuous attack of the adhesion during the laser surgery.

Another advantage of the present invention is that the utilization of the smoke evacuation bore removes the smoke produced in the peritoneal cavity during the laser surgery. In prior-art techniques, this smoke would tend to obscure or blur the image produced through the laparoscope. By the removal of the smoke during the surgical procedure, the laparoscopic image remains clear with less obscuration. The smoke will simply be drawn through the evacuation bore and from the peritoneal cavity.

The foregoing disclosure and description of the invention is illustrative and explanatory thereof, and various changes in the size, shape, and materials, as well as in the details of the illustrated construction, may be made within the scope of the appended claims without departing from the spirit of the invention. This invention should only be limited by the appended claims and their legal equivalents.

I claim:

1. A surgical laser backstop instrument comprising:
   a rod having a non-reflective surface;
   a backstop pivotally connected to one end of said rod, said backstop comprised of a non-reflecting material; and
   backstop adjustment means mounted to the other end of said rod, said backstop adjustment means for controlling the movement of said backstop.

2. The instrument of claim 1, said surface being a coating of non-reflective material.

3. The instrument of claim 2, said rod coated with titanium material.

4. The instrument of claim 2, said rod having a length of greater than twelve inches.

5. The instrument of claim 2, said rod having a diameter of thirteen/sixty-fourths of an inch or greater.

6. The instrument of claim 2, said rod having an evacuation bore extending longitudinally therethrough.

7. The instrument of claim 6, said surgical laser backstop instrument further comprising:
   smoke evacuation means connected to one end of said evacuation bore opposite said backstop, said smoke evacuation means for drawing smoke through said evacuation bore.

8. The instrument of claim 1, said backstop comprising a flat section of titanium-coated material having a width equal to or less than the diameter of said rod.

9. The instrument of claim 8, said backstop movable between a position in which said backstop is align with the longitudinal axis of said rod and a position in which the backstop is transverse to the longitudinal axis of said rod.

10. The instrument of claim 9, said backstop extending outwardly for a distance greater than seven-tenths of an inch from the end of said rod.

11. The instrument of claim 1, said backstop adjustment means comprising:
   a body connected to said other end of said rod;
   a line fastened at one end to said backstop and extending through said rod; and movement actuator means connected to the other end of said line, said movement actuator means connected to said body for controlling the pivotal movement of said backstop.

12. The instrument of claim 11, said body comprising a barrel having an aperture extending at least partially therethrough, said barrel fixedly attached to the other end of said rod.

13. The instrument of claim 11, said line comprising a wire connected at one end to said movement actuator means and at the other end to said backstop, said wire extending through a longitudinal bore in said rod.

14. The instrument of claim 13, said line comprising a pair of wires extending through parallel bores in said rod.

15. The instrument of claim 11, said movement actuator means comprising:
 - a knob rotatably mounted to said body, said knob for manually controlling the positioning of said backstop;
 - a rack assembly placed within said body and connected to the other end of said line; and
 - a pinion gear engaging said rack assembly and connected to said knob such that rotational movement of said knob causes a corresponding rotation of said pinion gear, said rack assembly movable relative to the rotational movement of said pinion gear.

16. The instrument of claim 11, said surgical laser backstop instrument further comprising:
 - smoke evacuation means connected to said body, said smoke evacuation means for drawing smoke from adjacent said backstop, said body having an aperture extending therethrough, said rod having an evacuation bore with an opening adjacent the pivotal connection of said backstop to said rod, said aperture of said body communicating with said evacuation bore, said smoke evacuation means including a vacuum connected external of said surgical laser backstop instrument.

17. A surgical laser backstop instrument comprising:
 - a rod comprised of an optically non-transmissive material;
 - a backstop pivotally mounted to one end of said rod, said backstop comprised of a laser non-reflective material; and
 - backstop adjustment means mounted at the other end of said rod, said backstop adjustment means for controlling the pivotal movement of said backstop relative to said rod.

18. The instrument of claim 17, said instrument further comprising:
 - smoke evacuation means extending through said rod, said smoke evacuation means for the removal of smoke at an area adjacent said backstop, said smoke evacuation means comprising:
   - a bore extending through the interior of said rod, said bore opening at the end of said rod adjacent said pivotal connection of said backstop with said rod; and
   - a vacuum pump communicating with said bore at the other end of said rod, said vacuum pump for drawing smoke through said bore.

* * * * *